US005780234A

United States Patent [19]
Meade et al.

[11] Patent Number: 5,780,234
[45] Date of Patent: *Jul. 14, 1998

[54] NUCLEIC ACID MEDIATED ELECTRON TRANSFER

[75] Inventors: Thomas J. Meade, Altadena; Jon Faiz Kayyem, Pasadena; Scott E. Fraser, Newport Beach, all of Calif.

[73] Assignee: California Institute of Technology, Pasadena, Calif.

[*] Notice: The term of this patent shall not extend beyond the expiration date of Pat. No. 5,591,578

[21] Appl. No.: 709,263

[22] Filed: Sep. 6, 1996

Related U.S. Application Data

[63] Continuation of Ser. No. 166,036, Dec. 10, 1993, Pat. No. 5,591,578.
[51] Int. Cl.$^6$ .............................. C12Q 1/68; C12Q 1/70; C07H 21/04; C07H 21/02
[52] U.S. Cl. .......................... 435/6; 435/5; 435/91.1; 435/91.2; 536/24.3; 536/24.32; 536/24.33; 536/23.1; 536/26.6
[58] Field of Search ..................... 435/91.2, 91.1, 435/6, 5; 536/24.3, 24.33, 24.32, 23.1, 26.6

[56] References Cited

U.S. PATENT DOCUMENTS

| | | | |
|---|---|---|---|
| 4,849,513 | 7/1989 | Smith et al. | 536/27 |
| 5,278,043 | 1/1994 | Bannwarth et al. | 536/23.1 |
| 5,565,552 | 10/1996 | Magda et al. | 534/11 |
| 5,573,906 | 11/1996 | Bannwarth et al. | 435/6 |
| 5,595,908 | 1/1997 | Fawcett et al. | 534/11 |

FOREIGN PATENT DOCUMENTS

| | | |
|---|---|---|
| 2090904 | 9/1993 | Canada . |
| 0 234 938 | 2/1987 | European Pat. Off. . |
| 0 229 943 | 7/1987 | European Pat. Off. . |
| 0599337 | 1/1994 | European Pat. Off. . |
| 63-238168 | 10/1988 | Japan . |
| WO9310267 | 5/1993 | WIPO . |
| 95/15971 | 12/1994 | WIPO . |

OTHER PUBLICATIONS

Arkin, M., et al., "Evidence for Photoelectron Transfer Through DNA Intercalation", Abstracts, p. 526.
Baum, R. M., "Views on Biological, Long–Range Electron Transfer Stir Debate", C&EN, pp. 20–23 (Feb. 22, 1993).
Bechtold, R., et al., "Ruthenium–Modified Horse Heart Cytochrome c: Effect of pH and Ligation on the Rate of Intramolecular Electron Transfer between Ruthenium(II) and Heme(III)", J. Phys. Chem., 90(16):3800–3804 (1986).
Farver, O., et al., "Long–range intramolecular electron transfer in azurins", Proc. Natl. Acad. Sci. USA, 86:6968–6972 (1989).
Bowler, B. E., et al., "Long–Range Electron Transfer in Donor (Spacer) Acceptor Molecules and Proteins", Progress in Inorganic Chemistry: Bioinorganic Chemistry, 38:259–322 (1990).

Brun, A. M., et al., "Photochemistry of Intercalated Quaternary Diazaaromatic Salts", J. Am. Chem. Soc., 113:8153–8159 (1991).
Chang, I–Jy, et al., "High–Driving–Force Electron Transfer in Metalloproteins: Intramolecular Oxidation of Ferrocytochrome c by Ru(2,2'–bpy)$_2$(im)(His–33)$^{3+}$", J. Am. Chem. Soc., 113:7056–7057 (1991).
Davis, L. M., et al., "Electron Donor Properties of the Antitumour Drug Amsacrine as Studied by Fluorescence Quenching of DNA–Bound Ethidium", Chem.–Biol. Interactions, 62:45–58 (1987).
Degani, Y., et al., "Electrical Communication between Redox Centers of Glucose Oxidase and Electrodes via Electrostatically and Covalently Bound Redox Polymers", J. Am. Chem. Soc., 111:2357–2358 (1989).
Degani, Y., et al., "Direct Electrical Comunication between Chemically Modified Enzymes and Metal Electrodes. 1. Electron Transfer from Glucose Oxidase to Metal Electrodes via Electron Relays, Bound Covalently to the Enzyme", J. Phys. Chem., 91(6):1285–1288 (1987).
Dreyer, G. B., et al., "Sequence–specific cleavage of single–stranded DNA: Oligodeoxynucleotide–EDTAbFE(II)", Proc. Natl. Acad. Sci. USA, 82:968–972 (1985).
Durham, B., et al., "Electron–Transfer Kinetics of Singly Labeled Ruthenium(II) Polpyridine Cytochrome c Derivatives", American Chemical Society, pp. 181–193 (1990).
Durham, B., et al., "Photoinduced Electron–Transfer Kinetics of Singly Labeled Ruthenium Bis(bipyridin) Dicarboxybipyridine Cytochrome c Derivatives", Biochemistry, 28:8659–8665 (1989).
Elias, H., et al., "Electron–Transfer Kinetics of Zn–Substituted Cytochrome c and Its Ru(NH$_3$)$_5$(Histidine–33) Derivative", J. Am. Chem. Soc., 110:429–434 (1988).
Fox, L. S., et al., "Gaussian Free–Energy Dependence of Electron–Transfer Rates in Iridium Complexes", Science, 247:1069–1071 (1990).
Fox, M. A., et al., "Light–Harvesting Polymer Systems", C&EN, pp. 38–48 (Mar. 15, 1993), vol. # not applicable.

(List continued on next page.)

*Primary Examiner*—W. Gary Jones
*Assistant Examiner*—Dianne Rees
*Attorney, Agent, or Firm*—Flehr Hohbach Test Albritton & Herbert LLP; Richard F. Trecartin; Robin M. Silva

[57] ABSTRACT

The present invention provides for the selective covalent modification of nucleic acids with redox active moieties such as transition metal complexes. Electron donor and electron acceptor moieties are covalently bound to the ribose-phosphate backbone of a nucleic acid at predetermined positions. The resulting complexes represent a series of new derivatives that are bimolecular templates capable of transferring electrons over very large distances at extremely fast rates. These complexes possess unique structural features which enable the use of an entirely new class of bioconductors and photoactive probes.

21 Claims, 4 Drawing Sheets

OTHER PUBLICATIONS

Francois, J–C., et al., "Periodic Cleavage of Poly(dA) by Oligothymidylates Covalently Linked to the 1,10–Phenanthroline–Copper Complex", Biochemistry, 27:2272–2276 (1988).

Friedman, A. E., et al., "Molecular 'Light Switch' for DNA: Ru(bpy)$_2$(dppz)$^{2+}$", J. Am. Chem. Soc., 112:4960–4962 (1990).

Fromherz, P., et al., "Photoinduced Electron Transfer in DNA Matrix from Intercalated Ethidium to Condensed Methylviologen", J. Am. Chem. Soc., 108:5361–5362 (1986).

Gregg, B. A., et al., "Redox Polymer Films Containing Enzymes. 1. A Redox–Conducting Epoxy Cement: Synthesis, Characterization, and Electrocatalytic Oxidation of Hydroquinone", J. Phys. Chem., 95:5970–5975 (1991).

Heller, A., et al., "Amperometric biosensors based on three–dimensional hydrogel–forming epoxy networks", Sensors and Actuators, 13–14:180–183 (1993).

Heller, A., "Electrical Wiring of Redox Enzymes", Acc. Chem. Res., 23:128–134 (1990).

Meade, T. J., "Driving–Force Effects on the Rate of Long–Range Electron Transfer in Ruthenium–Modified Cytochrome c", J. Am. Chem. Soc., 111:4353–4356 (1989).

Murphy, C. J., et al., "Long–Range Photoinduced Electron Transfer Through a DNA Helix", Science, 262:1025–1029 (1993).

Orellana, G., et al., "Photoinduced Electron Transfer Quenching of Excited Ru(II) Polypyridyls Bound to DNA: The Role of the Nucleic Acid Double Helix", Photochemistry and Photobiology, 54(4):499–509 (1991).

Purugganan, M. D., et al., Accelerated Electron Transfer Between Metal Complexes Mediated by DNA, Science, 241:1645–1649 (1988).

Ho "DNA–Mediatd Electron Transfer and Application to 'Biochip'Development," Abstract, Office of Naval Research (Report Date: Jul. 25, 1991) 1–4, RR04106.

Risser, S. M., et al., "Electron Transfer in DNA: Predictions of Exponential Growth and Decay of Coupling with Donor–Acceptor Distance", J. Am. Chem. Soc., 115(6):2508–2510 (1993).

Satyanarayana, S., et al., "Neither β–nor βTris(phenanthroline)ruthenium(II) Binds to DNA by Classical Intercalation", Biochemistry, 31(39):9319–9324 (1992).

Schuhmann, W., et al., "Electron Transfer between Glucose Oxidase and Electrodes via Redox Mediators Bound with Flexible Chains to the Enzyme Surface", J. Am. Chem. Soc., 113:1394–1397 (1991).

Strobel, S. A., et al., "Site–Specific Cleavage of a Yeast Chromosome by Oligonucleotide–Directed Triple–Helix Formation", Science, 249:73–75 (1990).

Dreyer, G. B., et al., "Sequence-specific cleavage of single–stranded DNA: Oligodeoxynucleotide–EDTAβFe(II)", Proc. Natl. Acad. Sci. USA, 82:968–972.

Telser, J., et al., "DNA Duplexes Covalently Labeled at Two Sites: Synthesis and Characterization by Steady–State and Time–Resolved Optical Spectroscopies", J. Am. Chem. Soc., 111:7226–7232 (1989).

Telser, J., et al., "DNA Oligomers and Duplexes Containing a Covalently Attached Derivative of Tris(2,2'–bipyridine)ruthenium(II): Synthesis and Characterization by Thermodynamic and Optical Spectroscopic Measurements", J. Am. Chem. Soc., 111:7221–7226 (1989).

Turro, N. J., et al., "Molecular Recognition and Chemistry in Restricted Reaction Spaces. Photophysics and Photoinduced Electron Transfer on the Surfaces of Micelles, Dendrimers, and DNA", Acc. Chem. Res., 24:332–340 (1991).

Winkler, J. R., et al., "Electron Transfer in Ruthenium–Modified Proteins", Chem. Rev., 92:369–379 (1992).

Murphy, C.J. et al., "Long–Range Photoinduced Electron Transfer Through a DNA Helix", Science, 262:1025–1029 (1993).

Boguslavsky, L. et al., "Applications of redox polymers in biosensors", Solid State Ionics, 60:189–197 (1993).

Millan, K.M. and Mikkelsen, S.R., "Sequence–Selective Biosensor for DNA Based on Electroactive Hybridization Indicators", Anal. Chem., 65: 2317–2323 (1993).

Cantor, C.R. et al., "Report on the Sequencing by Hybridization Workshop", Genomics, 13: 1378–1383 (1992).

Database WPI, Derwent Publications Ltd., London, GB; AN 88–320199 & JP, A, 53 238 166 (Mitsubishi Denki KK), 4 Oct. 1988.

Turro, N., et al. "Photoelectron Transfer Between Molecules Adsorbed in Restricted Spaces," Photochem. Convers. Storage Sol. Energy, Proc. Int. Conf., 8th 1990, pp. 121–139, vol # not applicable.

Degani et al., "Direct Electrical Communication between Chemically Modified Enzymes and Metal Electrodes. 2. Methods for Bonding Electron–Transfer Relays to Glucose Oxidase and D–Amino–Acid Oxidase," J. Am. Chem. Soc. 110:2615–2620 (1988).

Meade et al., "Electron Transfer through DNA: Site–Specific Modification of Duplex DNA with Ruthenium Donors and Acceptors," *Angew Chem. Int. Ed. Engl.* 34:352 (1995).

Chidsey, C.E.D., et al., "Free Engergy and Temperature Dependence of Electron Transfer at the Metal Electrolyte Interface", Science, 251:919–923 (1991).

Deinhammer, R.S., et al., "Electronchemical Oxidation of Amine–containing compounds: A Route to the Surface Modification of glassy carbon electrodes", Langmuir, 10:1306–1313 (1994).

Gregg, B.A., et al., "Cross–linked redox gels containing glucose oxidase for amperometric biosensor applications", Anal. Chem., 62:258–263 (1990).

Lenhard, J.R., et al., "Part VII Covalent Bonding of a Reversible Electrode Reactanbt to Pt Electrodes Using an organosilane Reagent" J. Electronal. Chem., 78:195–201 (1977).

Millan, K.M., et al., "Covalent Immobilization of DNA onto Glassy Carbon Electrodes", Electroanalysis, 4:929–932, (1992).

Miller, C., "Absorbed β–Hydroxy Thiol Monolayers on Gold Electrodes: Evidence for Electron Tunneling to Redox Species in Solution", J. Phys. Chem., 95:877–886 (1991).

Hobbs et al., "Polynucleotides Containing 2'–Amino–2'deoxyribose and 2'–Azido–2'–deoxyriose," Biochemistry, 12(25):5138–5145 (1973).

Jenkins et al., "A Sequence–Specific Molecular Light Switch: Tebhering of an Oligonucleotide to a Dipyridophenazine Complex of Ruthenium (II)" *J. Am. Chem. Soc.*, 114:8736–8738 (1992).

Kojima et al., "A DNA Probe of Ruthenium Bipyridine Complex Using Photocatalytic Activity," *Chemistry Letter*, 1889–1982 (1989).

Paterson, "Electric Genes: Current Flow in DNA Could Lead to Faster Genetic Testing," *Scientific American*, 33–34 (May 1995).

Clery, "DNA Goes Electric," *Science*, 267–1270 (Mar. 1995). vol. # not applicable.

Mestel, "'Electron Highway' Points to Identity of DNA," *New Scientist*, p. 21 (4 Mar. 1995). vol # not applicable.

Lipkin "Identifying DNA by the Speed of Electrons," *Science News*, 147(8)117 (Feb. 25, 1995).

"Biotechnology and Genetics: Genetic Screening Integrated Circuit," *The Economist*, (Feb. 25–Mar. 3, 1995). vol. # page # not applicable.

Mazzocchi, P.H. and G. Fritz, "Photolysis of N-(2-Methyl-2-Propenyl)phthalimide in Methanol. Evidence Supporting Radical–Radical Coupling of a Photochemically Generated Radical Ion Pair," *Journal of the American Chemical Society*, 108(17):5361–5362 (1986).

(I)   R¹ = H     R² = NH$_2$
(II)  R¹ = NH$_2$  R² = H
(III) R¹ = NH$_2$  R² = OH
(IV)  R¹ = OH    R² = NH$_2$
(Base) Adenine, guanine, cytosine, thymidine, uridine.

NUCLEIC ACID MEDIATED ELECTRON TRANSFER

This is a continuation of application Ser. No. 08/166,036 filed Dec. 10, 1993 now U.S. Pat. No. 5,591,578.

FIELD OF THE INVENTION

The present invention is directed to electron transfer via nucleic acids. More particularly, the invention is directed to the site-selective modification of nucleic acids with electron transfer moieties such as redox active transition metal complexes to produce a new series of biomaterials and to methods of making and using them. The novel biomaterials of the present invention may be used as bioconductors and diagnostic probes.

BACKGROUND OF THE INVENTION

The present invention, in part, relates to methods for the site-selective modification of nucleic acids with redox active moieties such as transition metal complexes, the modified nucleic acids themselves, and their uses. Such modified nucleic acids are particularly useful as bioconductors and photoactive nucleic acid probes.

The detection of specific nucleic acid sequences is an important tool for diagnostic medicine and molecular biology research. Gene probe assays currently play roles in identifying infectious organisms such as bacteria and viruses, in probing the expression of normal genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4: 48–51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4: 41–47 (1993)).

Specificity, in contrast, remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some limited circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation and probe digestion assays in which mismatches create sites for probe cleavage.

Finally, the automation of gene probe assays remains an area in which current technologies are lacking. Such assays generally rely on the hybridization of a labelled probe to a target sequence followed by the separation of the unhybridized free probe. This separation is generally achieved by gel electrophoresis or solid phase capture and washing of the target DNA, and is generally quite difficult to automate easily.

The time consuming nature of these separation steps has led to two distinct avenues of development. One involves the development of high-speed, high-throughput automatable electrophoretic and other separation techniques. The other involves the development of non-separation homogeneous gene probe assays.

For example, Gen-Probe Inc., (San Diego, Calif.) has developed a homogeneous protection assay in which hybridized probes are protected from base hydrolysis, and thus are capable of subsequent chemiluminescence. (Okwumabua et al. Res. Microbiol. 143: 183 (1992)). Unfortunately, the reliance of this approach on a chemiluminescent substrate known for high background photon emission suggests this assay will not have high specificity. EPO application number 86116652.8 describes an attempt to use non-radiative energy transfer from a donor probe to an acceptor probe as a homogeneous detection scheme. However, the fluorescence energy transfer is greatly influenced by both probe topology and topography, and the DNA target itself is capable of significant energy quenching, resulting in considerable variability. Therefore there is a need for DNA probes which are specific, capable of detecting target mismatches, and capable of being incorporated into an automated system for sequence identification.

As outlined above, molecular biology relies quite heavily on modified or labelled oligonucleotides for traditional gene probe assays (Oligonucleotide Synthesis: A Practical Approach. Gait et al., Ed., IRL Press: Oxford, UK, 1984; Oligonucleotides and Analogues: A Practical Approach. Ed. F. Eckstein, Oxford University Press, 1991). As a result, several techniques currently exist for the synthesis of tailored nucleic acid molecules. Since nucleic acids do not naturally contain functional groups to which molecules of interest may easily be attached covalently, methods have been developed which allow chemical modification at either of the terminal phosphates or at the heterocyclic bases (Dreyer et al. Proc. Natl. Acad. Sci. USA, 1985, 82: 968).

For example, analogues of the common deoxyribo- and ribonucleosides which contain amino groups at the 2' or 3' position of the sugar can be made using established chemical techniques. (See Imazawa et al., J. Org. Chem., 1979, 44: 2039; Imazawa et al., J. Org. Chem. 43(15): 3044 (1978); Verheyden et al., J. Org. Chem. 36(2): 250 (1971); Hobbs et al., J. Org. Chem. 42(4): 714 (1977)). In addition, oligonucleotides may be synthesized with 2'-5' or 3'-5' phosphoamide linkages (Beaucage et al., Tetrahedron 49(10): 1925 (1992); Letsinger, J. Org. Chem., 35: 3800 (1970); Sawai, Chem. Lett. 805 (1984); Oligonucleotides and Analogues: A Practical Approach. F. Eckstein. Ed. Oxford University Press (1991)).

The modification of nucleic acids has been done for two general reasons: to create nonradioactive DNA markers to serve as probes, and to use chemically modified DNA to obtain site-specific cleavage.

To this end, DNA may be labelled to serve as a probe by altering a nucleotide which then serves as a replacement analogue in the nick translational resynthesis of double stranded DNA. The chemically altered nucleotides may then provide reactive sites for the attachment of immunological or other labels such as biotin. (Gilliam et al., Anal. Biochem. 157: 199 (1986)). Another example uses ruthenium derivatives which intercalate into DNA to produce photoluminescence under defined conditions. (Friedman et al., J. Am. Chem. Soc. 112: 4960 (1990)).

In the second category, there are a number of examples of compounds covalently linked to DNA which subsequently cause DNA chain cleavage. For example 1,10-phenanthroline has been coupled to single-stranded oligothymidylate via a linker which results in the cleavage of poly-dA oligonucleotides in the presence of $Cu^{2+}$ and 3-mercaptopropionic acid (Francois et al., Biochemistry 27: 2272 (1988)). Similar experiments have been done for $EDTA^1$-Fe(II) (both for double stranded DNA (Boutorin et al., FEBS Lett. 172: 43–46 (1986)) and triplex DNA (Strobel et al., Science 249: 73 (1990)), porphyrin-Fe(III) (Le Doan et al., Biochemistry 25: 6736–6739 (1986)), and 1,10-phenanthronine-Cu(I) (Chen et al., Proc. Natl. Acad. Sci USA, 83: 7147 (1985)), which all result in DNA chain cleavage in the presence of a reducing agent in aerated solutions. A similar example using porphyrins resulted in DNA strand cleavage, and base oxidation or cross-linking of the DNA under very specific conditions (Le Doan et al., Nucleic Acids Res. 15: 8643 (1987)).

Other work has focused on chemical modification of heterocyclic bases. For example, the attachment of an inorganic coordination complex, Fe-EDTA, to a modified internal base resulted in cleavage of the DNA after hybridization in the presence of dioxygen (Dreyer et al., Proc. Natl. Acad. Sci. USA 82: 968 (1985)). A ruthenium compound has been coupled successfully to an internal base in a DNA octomer, with retention of both the DNA hybridization capabilities as well as the spectroscopic properties of the ruthenium label (Telser et al., J. Am. Chem. Soc. 111: 7221 (1989)). Other experiments have successfully added two separate spectroscopic labels to a single double-stranded DNA molecule (Telser et al., J. Am. Chem. Soc. 111: 7226 (1989)).

The study of electron transfer reactions in proteins and DNA has also been explored in pursuit of systems which are capable of long distance electron transfer.

To this end, intramolecular electron transfer in protein-protein complexes, such as those found in photosynthetic proteins and proteins in the respiration pathway, has been shown to take place over appreciable distances in protein interiors at biologically significant rates (see Bowler et al., Progress in Inorganic Chemistry: Bioinorganic Chemistry, Vol. 38, Ed. Stephen J. Lippard (1990). In addition, the selective modification of metalloenzymes with transition metals has been accomplished and techniques to monitor electron transfer in these systems developed. For example, electron transfer proteins such as cytochrome c have been modified with ruthenium through attachment at several histidines and the rate of electron transfer from the heme $Fe^{2+}$ to the bound $Ru^{3+}$ measured. The results suggest that electron transfer "tunnel" pathways may exist. (Baum, Chemical & Engineering News, Feb. 22, 1993, pages 2023; see also Chang et al., J. Am. Chem. Soc. 113: 7056 (1991)). In related work, the normal protein insulation, which protects the redox centers of an enzyme or protein from nondiscriminatory reactions with the exterior solvent, was "wired" to transform these systems from electrical insulators into electrical conductors (Heller, Acc. Chem. Res. 23: 128 (1990)).

There are a few reports of photoinduced electron transfer in a DNA matrix. In these systems, the electron donors and acceptors are not covalently attached to the DNA, but randomly associated with the DNA, thus rendering the explicit elucidation and control of the donor-acceptor system difficult. For example, the intense fluorescence of certain quaternary diazoaromatic salts is quenched upon intercalation into DNA or upon exposure to individual mononucleotides, thus exhibiting electron donor processes within the DNA itself. (Brun et al., J. Am. Chem. Soc. 113: 8153 (1991)).

Another example of the difficulty of determining the electron transfer mechanism is found in work done with some photoexcitable ruthenium compounds. Early work suggested that certain ruthenium compounds either randomly intercalate into the nucleotide bases, or bind to the helix surface. (Purugganan et al., Science 241: 1645 (1988)). A recent reference indicates that certain ruthenium compounds do not intercalate into the DNA (Satyanarayana et al., Biochemistry 31(39): 9319 (1992)); rather, they bind non-covalently to the surface of the DNA helix.

In these early experiments, various electron acceptor compounds, such as cobalt, chromium or rhodium compounds were added to certain DNA-associated ruthenium electron donor compounds. (Purugganan et al., Science 241: 1645 (1988); Orellana et al., Photochem. Photobiol. 499: 54 (1991); Brun et al., J. Am. Chem. Soc. 113: 8153 (1991); Davis, Chem.-Biol. Interactions 62: 45 (1987); Tomalia et al., Acc. Chem. Res., 24: 332 (1991)). Upon addition of these various electron acceptor compounds, which randomly bind non-covalently to the helix, quenching of the photoexcited state through electron transfer was detected. The rate of quenching was dependent on both the individual electron donor and acceptor as well as their concentrations, thus revealing the process as bimolecular.

In one set of experiments, the authors postulate that the more mobile surface bound donor promotes electron transfer with greater efficiency than the intercalated species, and suggest that the sugar-phosphate backbone of DNA, and possibly the solvent medium surrounding the DNA, play a significant role in the electron transport. (Purugganan et al., Science 241: 1645 (1988)). In other work, the authors stress the dependence of the rate on the mobility of the donor and acceptor and their local concentrations, and assign the role of the DNA to be primarily to facilitate an increase in local concentration of the donor and acceptor species on the helix. (Orellana et al., supra).

In another experiment, an electron donor was reportedly randomly intercalated into the stack of bases of DNA, while the acceptor was randomly associated with the surface of the DNA. The rate of electron transfer quenching indicated a close contact of the donor and the acceptor, and the system also exhibits enhancement of the rate of electron transfer with the addition of salt to the medium. (Fromherz et al., J. Am. Chem. Soc. 108: 5361 (1986)).

In all of these experiments, the rate of electron transfer for non-covalently bound donors and acceptors is several orders of magnitude less than is seen in free solution.

An important stimulus for the development of long distance electron transfer systems is the creation of synthetic light harvesting systems. Work to date suggests that an artificial light harvesting system contains an energy transfer complex, an energy migration complex, an electron transfer complex and an electron migration complex (for a topical review of this area, see Chemical & Engineering News, Mar. 15, 1993, pages 38–48). Two types of molecules have been tried: a) long organic molecules, such as hydrocarbons with covalently attached electron transfer species, or DNA, with intercalated, partially intercalated or helix associated electron transfer species, and b) synthetic polymers.

The long organic molecules, while quite rigid, are influenced by a number of factors, which makes development difficult. These factors include the polarity and composition of the solvent, the orientation of the donor and acceptor groups, and the chemical character of either the covalent linkage or the association of the electron transfer species to the molecule.

The creation of acceptable polymer electron transfer systems has been difficult because the available polymers are too flexible, such that several modes of transfer occur. Polymers that are sufficiently rigid often significantly interfere with the electron transfer mechanism or are quite difficult to synthesize.

Thus the development of an electron transfer system which is sufficiently rigid, has covalently attached electron transfer species at defined intervals, is easy to synthesize and does not appreciably interfere with the electron transfer mechanism would be useful in the development of artificial light harvesting systems.

In conclusion, the random distribution and mobility of the electron donor and acceptor pairs, coupled with potential short distances between the donor and acceptor, the loose and presumably reversible association of the donors and acceptors, the reported dependence on solvent and broad putative electron pathways, and the disruption of the DNA structure of intercalated compounds rendering normal base pairing impossible all serve as pronounced limitations of long range electron transfer in a DNA matrix. Therefore, a method for the production of rigid, covalent attachment of electron donors and acceptors to provide minimal perturbations of the nucleic acid structure and retention of its ability to base pair normally, is desirable. The present invention serves to provide such a system, which allows the development of novel bioconductors and diagnostic probes.

SUMMARY OF THE INVENTION

The present invention provides for the selective modification of nucleic acids at specific sites with redox active moieties such as transition metal complexes. An electron donor and/or electron acceptor moiety are covalently bound preferably along the ribose-phosphate backbone of the nucleic acid at predetermined positions. The resulting complexes represent a series of new derivatives that are biomolecular templates capable of transferring electrons over very large distances at extremely fast rates. These complexes possess unique structural features which enable the use of an entirely new class of bioconductors and diagnostic probes.

Accordingly, it is an object of the invention to provide a single stranded nucleic acid which has both an electron donor moiety and an electron acceptor moiety covalently attached thereto. These moieties are attached through the ribose phosphate or analogous backbone of the nucleic acid. The single stranded nucleic acid is capable of hybridizing to a complementary target sequence in a single stranded nucleic acid, and transferring electrons between the donor and acceptor.

It is a further object of the present invention to provide for a nucleic acid probe which can detect base-pair mismatches. In this embodiment, the single stranded nucleic acid with a covalently attached electron donor and electron acceptor moiety is hybridized to a complementary target sequence in a single stranded nucleic acid. When the region of hybridization contains at least one base pair mismatch, the rate of electron transfer between the donor moiety and the acceptor moiety is decreased or eliminated, as compared to when there is perfect complementarity between the probe and target sequence.

It is an additional object of the present invention to provide a complex which contains a first single stranded nucleic acid with at least one electron donor moiety and a second single stranded nucleic acid with at least one electron acceptor moiety. As with the other embodiments of the present invention, the moieties are covalently linked to the ribose-phosphate backbone of the nucleic acids.

In one aspect of the present invention, the first and second single stranded nucleic acids are capable of hybridizing to each other to form a double stranded nucleic acid, and of transferring electrons between the electron donor moiety and the electron acceptor moiety.

In another aspect of the present invention, a target sequence in a single stranded nucleic acid comprises at least first and second target domains, which are directly adjacent to one another. The first single stranded nucleic acid hybridizes to the first target domain and the second single stranded nucleic acid hybridizes to the second target domain, such that the first and second single stranded nucleic acids are adjacent to each other. This resulting hybridization complex is capable of transferring electrons between the electron donor moiety and the electron acceptor moiety on the first and second nucleic acids.

In another aspect of the present invention, a target sequence in a single stranded nucleic acid comprises a first target domain, an intervening target domain, and a second target domain. The intervening target domain comprises one or more nucleotides. The first and second single stranded nucleic acids hybridize to the first and second target domains. An intervening nucleic acid comprising one or more nucleotides hybridizes to the target intervening domain such that electrons are capable of being transferred between the electron donor moiety and the electron acceptor moiety on the first and second nucleic acids.

The invention also provides for a method of making a single stranded nucleic acid containing an electron transfer moiety covalently attached to the 5' terminus of the nucleic acid. The method comprises incorporating a modified nucleotide into a growing nucleic acid at the 5' position to form a modified single stranded nucleic acid. The modified single stranded nucleic acid is then hybridized with a complementary single stranded nucleic acid to form a double stranded nucleic acid. The double stranded nucleic acid is reacted with an electron transfer moiety such that the moiety is covalently attached to the modified single stranded nucleic acid. The modified single stranded nucleic acid containing the electron transfer moiety is separated from the complementary unmodified single stranded nucleic acid.

The present invention also provides a method for making a single stranded nucleic acid containing an electron transfer moiety covalently attached to an internal nucleotide. The method comprises creating a nucleotide dimer joined by a phosphoramide bond and incorporating said nucleotide dimer into a growing nucleic acid to form a modified single stranded nucleic acid. The modified single stranded nucleic acid is then hybridized with a complementary single stranded nucleic acid to form a double stranded nucleic acid. The double stranded nucleic acid is reacted with an electron transfer moiety such that the moiety is covalently attached to the modified single stranded nucleic acid. The modified single stranded nucleic acid containing the electron transfer moiety is separated from the complementary unmodified single stranded nucleic acid.

Another aspect of the present invention provides a method of detecting a target sequence. The method comprises creating a single stranded nucleic acid with an electron donor moiety and an electron acceptor moiety covalently attached. The single stranded nucleic acid containing the electron transfer moieties is then hybridized to the target sequence, and an electron transfer rate determined between the electron donor and the electron acceptor.

BRIEF DESCRIPTION OF THE DRAWINGS

FIGS. 2A1-A9, B1-B9 illustrate orientations of electron transfer moieties EDM and EAM on two adjacent single stranded nucleic acids. These orientations also apply when the two probes are separated by an intervening sequence.

FIGS. 4A and 4B depict the structure of electron transfer moieties.

DETAILED DESCRIPTION

Unless otherwise stated, the term "nucleic acid" or "oligonucleotide" or grammatical equivalents herein means at least two nucleotides covalently linked together. A nucleic acid of the present invention will generally contain phosphodiester bonds, although in some cases, as outlined below, a nucleic acid may have an analogous backbone, comprising, for example, phosphoramide (Beaucage et al., Tetrahedron 49(10): 1925 (1993) and references therein; Letsinger, J. Org. Chem. 35: 3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114: 1895 (1992); Meier et al., Chem. Int. Ed. Engl. 31: 1008 (1992); Nielsen, Nature, 365: 566 (1993)). The nucleic acids may be single stranded or double stranded, as specified. The nucleic acid may be DNA, RNA or a hybrid, where the nucleic acid contains any combination of deoxyribo- and ribo-nucleotides, and any combination of uracil, adenine, thymine, cytosine and guanine. In some instances, e.g. in the case of an "intervening nucleic acid", the term nucleic acid refers to one or more nucleotides.

The terms "electron donor moiety", "electron acceptor moiety", and "electron transfer moieties" or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. Generally, electron transfer moieties contain transition metals as components, but not always.

The term "target sequence" or grammatical equivalents herein means a nucleic acid sequence on a single strand of nucleic acid. The target sequence may be a portion of a gene, a regulatory sequence, genomic DNA, mRNA, or others. It may be any length, with the understanding that longer sequences are more specific. Generally speaking, this term will be understood by those skilled in the art.

The probes of the present invention are designed to be complementary to the target sequence, such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence.

The terms "first target domain" and "second target domain" or grammatical equivalents herein means two portions of a target sequence within a nucleic acid which is under examination. The first target domain may be directly adjacent to the second target domain, or the first and second target domains may be separated by an intervening target domain. The terms "first" and "second" are not meant to confer an orientation of the sequences with respect to the 5'-3' orientation of the target sequence. For example, assuming a 5'-3' orientation of the complementary target sequence, the first target domain may be located either 5' to the second domain, or 3' to the second domain.

The present invention is directed, in part, to the site-selective modification of nucleic acids with redox active moieties such as transition metal complexes for the preparation of a new series of biomaterials capable of long distance electron transfer through a nucleic acid matrix. The present invention provides for the precise placement of electron transfer donor and acceptor moieties at predetermined sites on a single stranded or double stranded nucleic acid. In general, electron transfer between electron donor and acceptor moieties in a double helical nucleic acid does not occur at an appreciable rate unless nucleotide base pairing exists in the sequence between the electron donor and acceptor in the double helical structure.

This differential in the rate of electron transfer forms the basis of a utility of the present invention for use as probes. In the system of the present invention, where electron transfer moieties are covalently bound to the backbone of a nucleic acid, the electrons putatively travel via the π-orbitals of the stacked base pairs of the double stranded nucleic acid. The electron transfer rate is dependent on several factors, including the distance between the electron donor-acceptor pair, the free energy ($\Delta G$) of the reaction, the reorganization energy ($\lambda$), the contribution of the intervening medium, the orientation and electronic coupling of the donor and acceptor pair, and the hydrogen bonding between the bases. The latter confers a dependence on the actual nucleic acid sequence, since A-T pairs contain one less hydrogen bond than C-G pairs. However, this sequence dependence is overshadowed by the determination that there is a measurable difference between the rate of electron transfer within a DNA base-pair matrix, and the rate through the ribose-phosphate backbone, the solvent or other electron tunnels. This rate differential is thought to be at least several orders of magnitude, and may be as high as four orders of magnitude greater through the stacked nucleotide bases as compared to other electron transfer pathways. Thus the presence of double stranded nucleic acids, for example in gene probe assays, can be determined by comparing the rate of electron transfer for the unhybridized probe with the rate for hybridized probes.

In one embodiment, the present invention provides for novel gene probes, which are useful in molecular biology and diagnostic medicine. In this embodiment, single stranded nucleic acids having a predetermined sequence and covalently attached electron donor and electron acceptor moieties are synthesized. The sequence is selected based upon a known target sequence, such that if hybridization to a complementary target sequence occurs in the region between the electron donor and the electron acceptor, electron transfer proceeds at an appreciable and detectable rate. Thus, the present invention has broad general use, as a new form of labelled gene probe. In addition, since detectable electron transfer in unhybridized probes is not appreciable, the probes of the present invention allow detection of target sequences without the removal of unhybridized probe. Thus, the present invention is uniquely suited to automated gene probe assays.

The present invention also finds use as a unique methodology for the detection of mutations in target nucleic acid sequences. As a result, if a single stranded nucleic acid containing electron transfer moieties is hybridized to a target sequence with a mutation, the resulting perturbation of the base pairing of the nucleotides will measurably affect the electron transfer rate. This is the case if the mutation is a substitution, insertion or deletion. Accordingly, the present invention provides for the detection of mutations in target sequences.

Thus, the present invention provides for extremely specific and sensitive probes, which may, in some embodiments, detect target sequences without removal of unhybridized probe. This will be useful in the generation of automated gene probe assays.

In an alternate embodiment double stranded nucleic acids have covalently attached electron donor and electron acceptor moieties on opposite strands. Such nucleic acids are useful to detect successful gene amplification in polymerase chain reactions (PCR). For example, if one of the two PCR primers contains a 5' terminally attached electron donor, and the other contains a 5' terminally attached electron acceptor, several rounds of PCR will generate doubly labeled double stranded fragments (occasionally referred to as "amplicons"). After appropriate photoinduction, the detection of electron transfer provides an indication of the successful amplification of the target sequence as compared to when no amplification occurs. A particular advantage of the present invention is that the separation of the single stranded primers from the amplified double stranded DNA is not necessary, as outlined above for probe sequences which contain electron transfer moieties.

In another embodiment the present invention provides for double stranded nucleic acids with covalently attached electron donor and electron acceptor moieties to serve as bioconductors or "molecular wire". The electron transport may occur over distances up to and in excess of 28 Å per electron donor and acceptor pair. In addition, the rate of electron transfer is very fast, even though dependent on the distance between the electron donor and acceptor moieties. By modifying the nucleic acid in regular intervals with electron donor and/or electron acceptor moieties, it may be possible to transport electrons over long distances, thus creating bioconductors. These bioconductors are useful in a large number of applications, including traditional applications for conductors such as mediators for electrochemical reactions and processes.

In addition, these bioconductors may be useful as probes for photosynthesis reactions as well as in the construction of synthetic light harvesting systems. The current models for the electron transfer component of an artificial light harvesting system have several problems, as outlined above, including a dependence on solvent polarity and composition, and a lack of sufficient rigidity without arduous synthesis. Thus the present invention is useful as both a novel form of bioconductor as well as a novel gene probe.

In addition, the present invention provides a novel method for the site specific addition to the ribose-phosphate backbone of a nucleic acid of electron donor and electron acceptor moieties to a previously modified nucleotide.

In one embodiment, the electron donor and acceptor moieties are added to the 3' and/or 5' termini of the nucleic acid. In alternative embodiments, the electron donor and acceptor moieties are added to the backbone of one or more internal nucleotides, that is, any nucleotide which is not the 3' or 5' terminal nucleotide. In a further embodiment, the electron donor and acceptor moieties are added to the backbone of both internal and terminal nucleotides.

In a preferred embodiment, the transition metal electron transfer moieties are added through a procedure which utilizes modified nucleotides, preferably amino-modified nucleotides. In this embodiment, the electron transfer moieties are added to the sugar phosphate backbone through the nitrogen group in phosphoramide linkages. The modified nucleotides are then used to site-specifically add a transition metal electron transfer moiety, either to the 3' or 5' termini of the nucleic acid, or to any internal nucleotide.

Figure 4A:
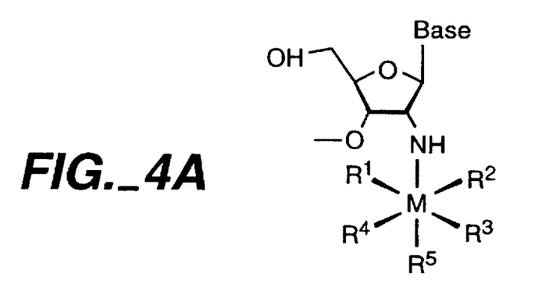
FIG. 4A depicts the general formula of a representative class of electron donors and acceptors.

Molecular mechanics calculations indicate that perturbations due to the modification of the terminal nucleotides of nucleic acids are minimal and Watson-Crick base pairing is not disrupted (unpublished data using Biograf from Molecular Simulations Inc., San Diego, Calif.). Accordingly, in one embodiment, modified nucleotides are used to add an electron transfer moiety to the 5' terminus of a nucleic acid. In this embodiment, the 2' position of the ribose of the deoxyribo- or ribonucleoside is modified prior to the addition of the electron transfer species, leaving the 3' position of the ribose unmodified for subsequent chain attachment. In a preferred embodiment, an amino group is added to the 2' carbon of the sugar using established chemical techniques. (Imazawa et al., J. Org. Chem., 44: 2039 (1979); Hobbs et al., J. Org. Chem. 42(4): 714 (1977); Verheyden et al. J. Org. Chem. 36(2): 250 (1971)). When the transition metal complex is attached to a ribose moiety modified with an amine group at the 2' position, there are four unconjugated sigma σ bonds between the metal and the base. As shown in FIG. 4A, the four unconjugated (σ) bonds are (1) the metal to nitrogen bond; (2) the nitrogen to 2' carbon bond; (3) the 2' carbon to 1' carbon bond; and (4) the 1' carbon to the base bond.

Once the modified nucleotides are prepared, protected and activated, they may be incorporated into a growing oligonucleotide by standard synthetic techniques (Gait, Oligonucleotide Synthesis: A Practical Approach, IRL Press, Oxford, UK 1984; Eckstein) as the 5' terminal nucleotide. This method therefore allows the addition of a transition metal electron transfer moiety to the 5' terminus of a nucleic acid.

In an alternative embodiment, the 3' terminal nucleoside is modified in order to add a transition metal electron transfer moiety. In this embodiment, the 3' nucleoside is modified at either the 2' or 3' carbon of the ribose sugar. In a preferred embodiment, an amino group is added to the 2' or 3' carbon of the sugar using established chemical techniques (Imazawa et al., J. Org. Chem., 44: 2039 (1979); Hobbs et al., J. Org. Chem. 42(4): 714 (1977); Verheyden et al. J. Org. Chem. 36(2): 250 (1971)). When the transition metal complex is attached to a ribose moiety modified with an amine group at the 3' position there are five unconjugated sigma (σ) bonds between the metal to the base. As shown in FIG. 4A, the five unconjugated σ bonds are (1) the metal to nitrogen bond; (2) the nitrogen to 3' carbon bond; (3) the 3' carbon to 2' carbon bond; (4) the 2' carbon to 1' carbon bond; and (5) the 1' carbon to the base bond.

Figure 1A:
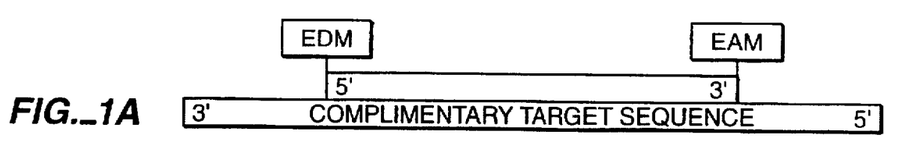
FIG. 1A–H illustrates possible orientations of electron donor (EDM) and electron acceptor (EAM) moieties on a single stranded nucleic acid.
Figure 1B:
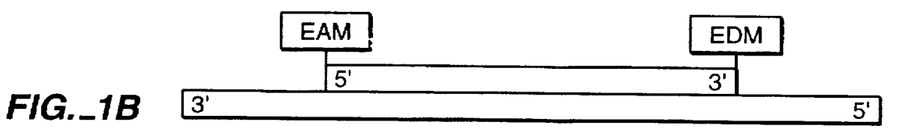
Figure 1C:
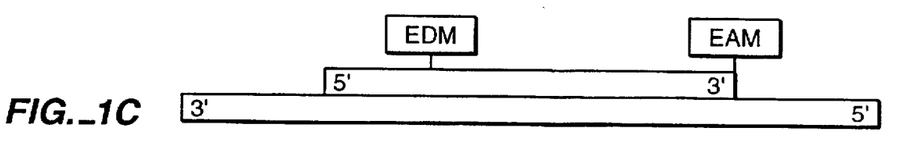
Figure 1D:
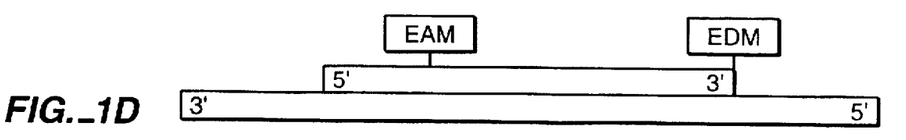
Figure 1E:
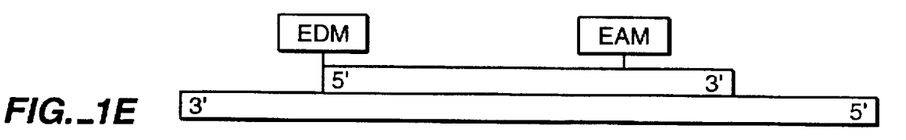
Figure 1F:
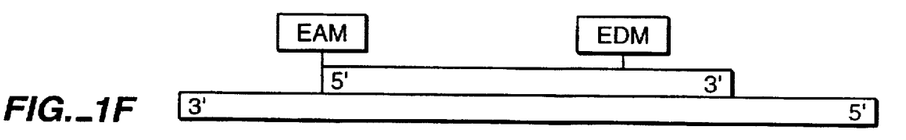
Figure 1G:
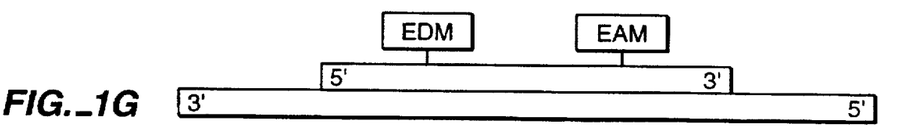
Figure 1H:
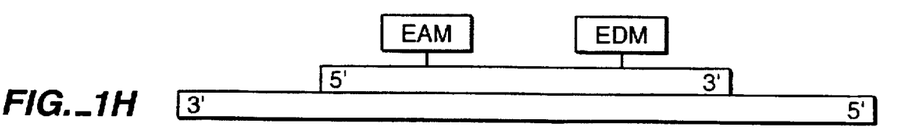
Figure 2:
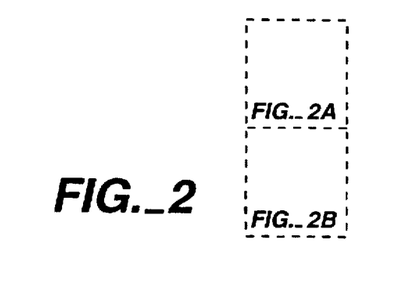
FIG. 2 is a schematic diagram of FIGS. 2A and 2B.
Figure 2A:
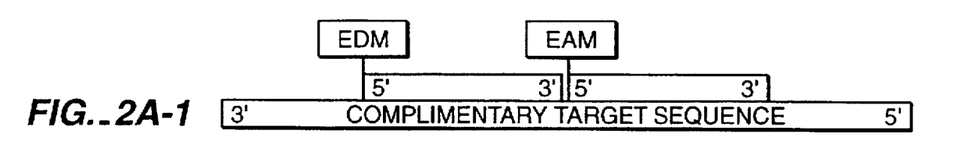
Figure 2A:
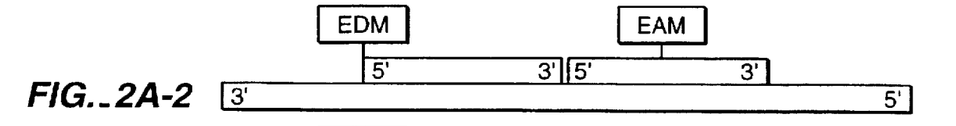
Figure 2A:
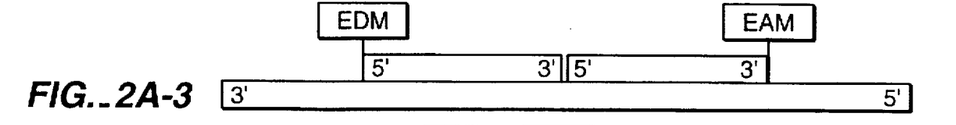
Figure 2A:
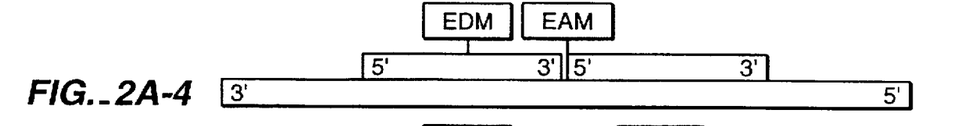
Figure 2A:
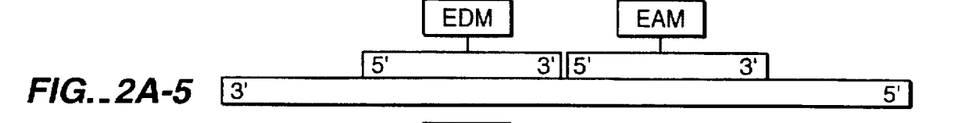
Figure 2A:
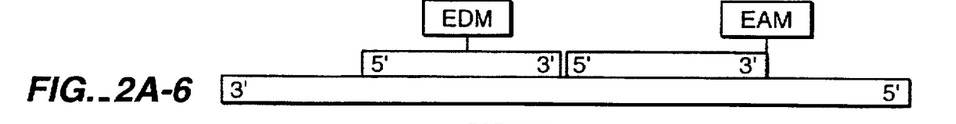
Figure 2A:
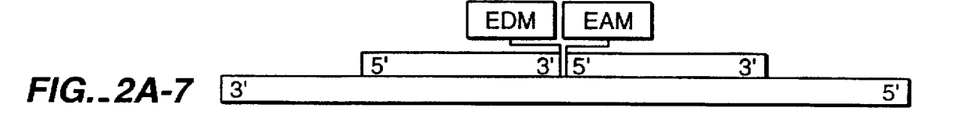
Figure 2A:
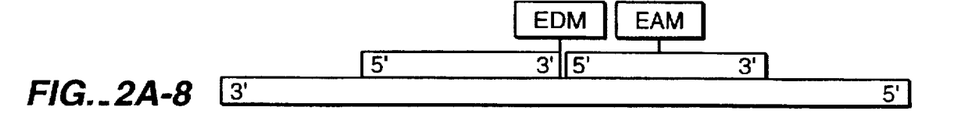
Figure 2A:
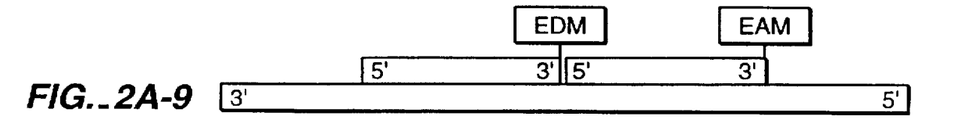
Figure 2B:
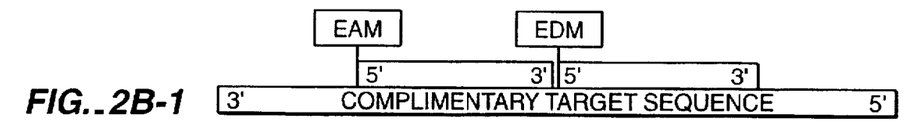
Figure 2B:
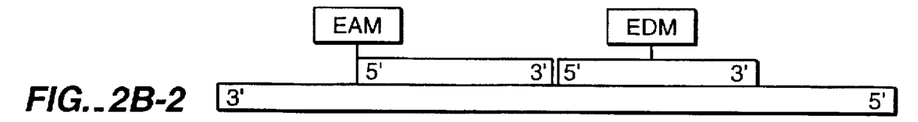
Figure 2B:
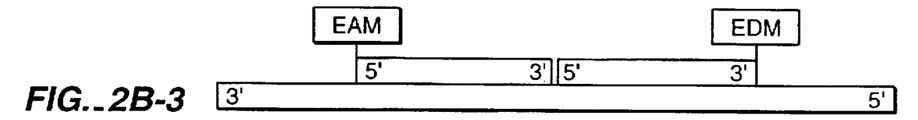
Figure 2B:
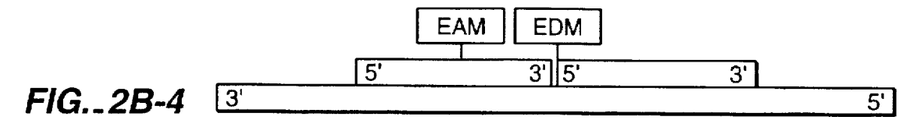
Figure 2B:
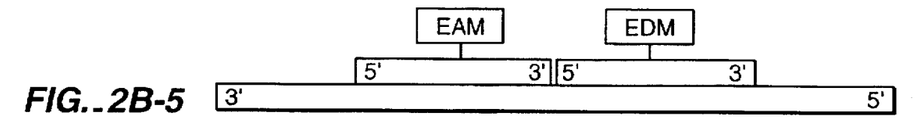
Figure 2B:
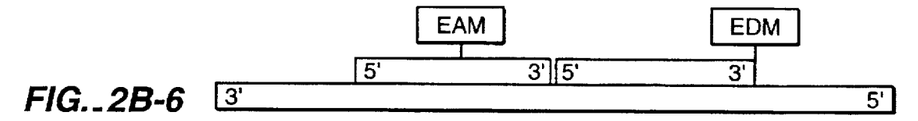
Figure 2B:
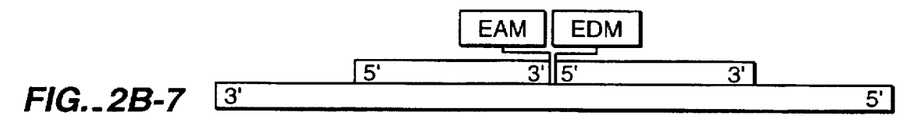
Figure 2B:
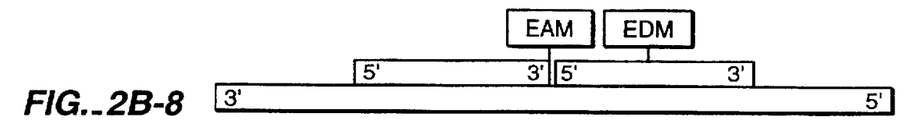
Figure 2B:
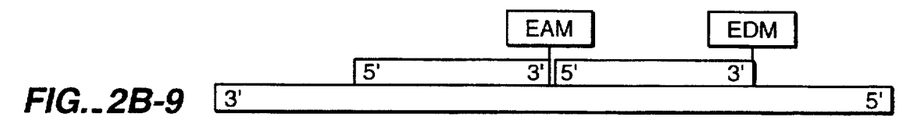
Figure 3:
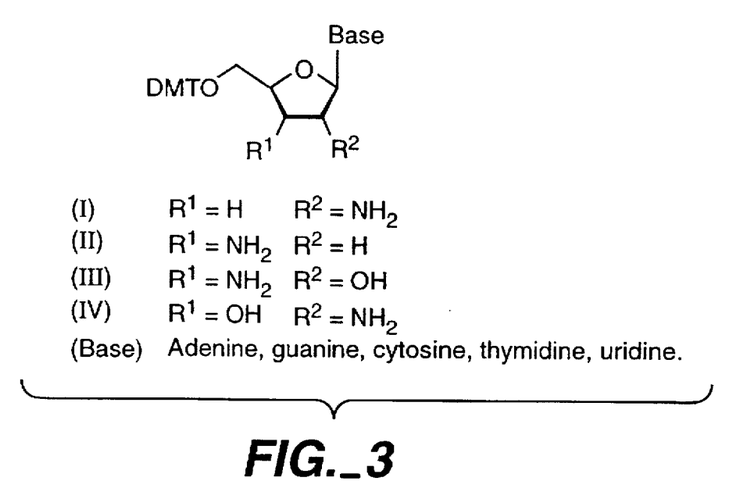
FIG. 3 illustrates a series of amino-modified nucleoside precursors prior to incorporation into an oligonucleotide.

The above procedures are applicable to both DNA and RNA derivatives as shown in FIG. 3.

The amino-modified nucleotides made as described above are converted to the 2' or 3' modified nucleotide triphosphate form using standard biochemical methods (Fraser et al., Proc. Natl. Acad. Sci. USA, 4: 2671 (1973)). One or more modified nucleosides are then attached at the 3' end using standard molecular biology techniques such as with the use of the enzyme DNA polymerase I or terminal deoxynucleotidyltransferase (Ratliff, Terminal deoxynucleotidyltransferase. In The Enzymes, Vol 14A. P. D. Boyer ed. pp 105–118, Academic Press, San Diego, Calif. 1981).

In other embodiments, the transition metal electron transfer moiety or moieties are added to the middle of the nucleic acid, i.e. to an internal nucleotide. This may be accomplished in three ways.

In a preferred embodiment, an oligonucleotide is amino-modified at the 5' terminus as described above. In this embodiment, oligonucleotide synthesis simply extends the 5' end from the amino-modified nucleotide using standard techniques. This results in an internally amino modified oligonucleotide.

In an alternate embodiment, electron transfer moieties are added to the backbone at a site other than ribose. For example, phosphoramide rather than phosphodiester linkages can be used as the site for transition metal modification. These transition metals serve as the donors and acceptors for electron transfer reactions. While structural deviations from native phosphodiester linkages do occur and have been studied using CD and NMR (Heller, Acc. Chem. Res. 23: 128 (1990); Schuhmann et al. J. Am. Chem. Soc. 113: 1394 (1991)), the phosphoramidite internucleotide link has been reported to bind to complementary polynucleotides and is stable (Beaucage et al., supra, and references therein; Letsinger, supra; Sawai, supra; Jager, Biochemistry 27: 7237 (1988)). In this embodiment, dimers of nucleotides are created with phosphoramide linkages at either the 2'-5' or 3'-5' positions. A preferred embodiment utilizes the 3'-5' position for the phosphoramide linkage, such that structural disruption of the subsequent Watson-Crick basepairing is minimized. These dimer units are incorporated into a growing oligonucleotide chain, as above, at defined intervals, as outlined below.

It should be noted that when using the above techniques for the modification of internal residues it is possible to create a nucleic acid that has an electron transfer species on the next-to-last 3' terminal nucleotide, thus eliminating the need for the extra steps required to produce the 3' terminally labelled nucleotide.

In a further embodiment for the modification of internal residues, 2' or 3' modified nucleoside triphosphates are generated using the techniques described above for the 3' nucleotide modification. The modified nucleosides are inserted internally into nucleic acid using standard molecular biological techniques for labelling DNA and RNA. Enzymes used for said labelling include DNA polymerases such as polymerase I, T4 DNA polymerase, T7 DNA polymerase, Taq DNA polymerase, reverse transcriptase and RNA polymerases such as E. coli RNA polymerase or the RNA polymerases from phages SP6, T7 or T3 (Short Protocols in Molecular Biology, 1992, Ausubel et al. Ed. pp 3.11–3.30).

In a preferred embodiment, the electron donor and acceptor moieties are attached to the modified nucleotide by methods which utilize a unique protective hybridization step. In this embodiment, the modified single strand nucleic acid is hybridized to an unmodified complementary sequence. This blocks the sites on the heterocyclic bases that are susceptible to attack by the transition metal electron transfer species. The exposed amine or other ligand at the 2' or 3' position of the ribose, the phosphoramide linkages, or the other linkages useful in the present invention, are readily modified with a variety of transition metal complexes with techniques readily known in the art (see for example Millet et al. in Metals in Biological Systems, Sigel et al. Ed. Vol. 27, pp 223–264, Marcell Dekker Inc. New York, 1991 and Durham, et al. in ACS Advances in Chemistry Series, Johnson et al. Eds., Vol. 226, pp 180–193, American Chemical Society, Washington D.C.; and Meade et al., J. Am. Chem. Soc. 111: 4353 (1989)). After successful addition of the desired metal complex, the modified duplex nucleic acid is separated into single strands using techniques well known in the art.

In a preferred embodiment, single stranded nucleic acids are made which contain one electron donor moiety and one electron acceptor moiety. The electron donor and electron acceptor moieties may be attached at either the 5' or 3' end of the single stranded nucleic acid. Alternatively, the electron transfer moieties may be attached to internal nucleotides, or one to an internal nucleotide and one to a terminal nucleotide. It should be understood that the orientation of the electron transfer species with respect to the 5'-3' orientation of the nucleic acid is not determinative. Thus, as outlined in FIG. 1, any combination of internal and terminal nucleotides may be utilized in this embodiment.

In an alternate preferred embodiment, single stranded nucleic acids with at least one electron donor moiety and at least one electron acceptor moiety are used to detect mutations in a complementary target sequence. A mutation, whether it be a substitution, insertion or deletion of a nucleotide or nucleotides, results in incorrect base pairing in a hybridized double helix of nucleic acid. Accordingly, if the path of an electron from an electron donor moiety to an electron acceptor moiety spans the region where the mismatch lies, the electron transfer will be eliminated or reduced such that a change in the relative rate will be seen. Therefore, in this embodiment, the electron donor moiety is attached to the nucleic acid at a 5' position from the mutation, and the electron acceptor moiety is attached at a 3' position, or vice versa.

In this embodiment it is also possible to use an additional label on the modified single stranded nucleic acid to detect hybridization where there is one or more mismatches. If the complementary target nucleic acid contains a mutation, electron transfer is reduced or eliminated. To act as a control, the modified single stranded nucleic acid may be radio- or fluorescently labeled, such that hybridization to the target sequence may be detected, according to traditional molecular biology techniques. This allows for the determination that the target sequence exists but contains a substitution, insertion or deletion of one or more nucleotides. Alternatively, single stranded nucleic acids with at least one electron donor moiety and one electron acceptor moiety which hybridize to regions with exact matches can be used as a controls for the presence of the target sequence.

It is to be understood that the rate of electron transfer through a double stranded nucleic acid helix depends on the nucleotide distance between the electron donor and acceptor moieties. Longer distances will have slower rates, and consideration of the rates will be a parameter in the design of probes and bioconductors. Thus, while it is possible to measure rates for distances in excess of 100 nucleotides, a preferred embodiment has the electron donor moiety and the electron acceptor moiety separated by at least 3 and no more than 100 nucleotides. More preferably the moieties are separated by 8 to 64 nucleotides, with 15 being the most preferred distance.

In addition, it should be noted that certain distances may allow the utilization of different detection systems. For example, the sensitivity of some detection systems may allow the detection of extremely fast rates; i.e. the electron transfer moieties may be very close together. Other detection systems may require slightly slower rates, and thus allow the electron transfer moieties to be farther apart.

In an alternate embodiment, a single stranded nucleic acid is modified with more than one electron donor or acceptor moiety. For example, to increase the signal obtained from these probes, or decrease the required detector sensitivity, multiple sets of electron donor-acceptor pairs may be used.

As outlined above, in some embodiments different electron transfer moieties are added to a single stranded nucleic acid. For example, when an electron donor moiety and an electron acceptor moiety are to be added, or several different electron donors and electron acceptors, the synthesis of the single stranded nucleic acid proceeds in several steps. First partial nucleic acid sequences are made, each containing a single electron transfer species, i.e. either a single transfer moiety or several of the same transfer moieties, using the techniques outlined above. Then these partial nucleic acid sequences are ligated together using techniques common in the art, such as hybridization of the individual modified partial nucleic acids to a complementary single strand, followed by ligation with a commercially available ligase.

In a preferred embodiment, single stranded nucleic acids are made which contain one electron donor moiety or one electron acceptor moiety. The electron donor and electron acceptor moieties are attached at either the 5' or 3' end of the single stranded nucleic acid. Alternatively, the electron transfer moiety is attached to an internal nucleotide.

It is to be understood that different species of electron donor and acceptor moieties may be attached to a single stranded nucleic acid. Thus, more than one type of electron donor moiety or electron acceptor moiety may be added to any single stranded nucleic acid.

In a preferred embodiment, a first single stranded nucleic acid is made with on or more electron donor moieties attached. A second single stranded nucleic acid has one or more electron acceptor moieties attached. In this embodiment, the single stranded nucleic acids are made for use as probes for a complementary target sequence. In one embodiment, the complementary target sequence is made up of a first target domain and a second target domain, where the first and second sequences are directly adjacent to one another. In this embodiment, the first modified single stranded nucleic acid, which contains only electron donor moieties or electron acceptor moieties but not both, hybridizes to the first target domain, and the second modified single stranded nucleic acid, which contains only the corresponding electron transfer species, binds to the second target domain. The relative orientation of the electron transfer species is not important, as outlined in FIG. 2, and the present invention is intended to include all possible orientations.

In the design of probes comprised of two single stranded nucleic acids which hybridize to adjacent first and second target sequences, several factors should be considered. These factors include the distance between the electron donor moiety and the electron acceptor moiety in the hybridized form, and the length of the individual single stranded probes. For example, it may be desirable to synthesize only 5' terminally labelled probes. In this case, the single stranded nucleic acid which hybridizes to the first sequence may be relatively short, such that the desirable distance between the probes may be accomplished. For example, if the optimal distance between the electron transfer moieties is 15 nucleotides, then the first probe may be 15 nucleotides long.

In one aspect of this embodiment, the two single stranded nucleic acids which have hybridized to the adjacent first and second target domains are ligated together prior to the electron transfer reaction. This may be done using standard molecular biology techniques utilizing a DNA ligase, such as T4 DNA ligase.

In an alternative embodiment, the complementary target sequence will have a first target domain, an intervening target domain, and a second target domain. In this embodiment, the first modified single stranded nucleic acid, which contains only electron donor moieties or electron acceptor moieties but not both, hybridizes to the first target domain, and the second modified single stranded nucleic acid, which contains only the corresponding electron transfer species, binds to the second target domain. When an intervening single stranded nucleic acid hybridizes to the intervening target sequence, electron transfer between the donor and acceptor is possible. The intervening sequence may be any length, and may comprise a single nucleotide. Its length, however, should take into consideration the desirable distances between the electron donor and acceptor moieties on the first and second modified nucleic acids. Intervening sequences of lengths greater than 14 are desirable, since the intervening sequence is more likely to remain hybridized to form a double stranded nucleic acid if longer intervening sequences are used. The presence or absence of an intervening sequence can be used to detect insertions and deletions.

In one aspect of this embodiment, the first single stranded nucleic acid hybridized to the first target domain, the intervening nucleic acid hybridized to the intervening domain, and the second single stranded nucleic acid hybridized to the second target domain, may be ligated together prior to the electron transfer reaction. This may be done using standard molecular biology techniques. For example, when the nucleic acids are DNA, a DNA ligase, such as T4 DNA ligase can be used.

The complementary target single stranded nucleic acid of the present invention may take many forms. For example, the complementary target single stranded nucleic acid sequence may be contained within a larger nucleic acid sequence, i.e. all or part of a gene or mRNA, a restriction fragment of a plasmid or genomic DNA, among others. One skilled in the art of molecular biology would understand how to construct useful probes for a variety of target sequences using the present invention.

In one embodiment, two single stranded nucleic acids with covalently attached electron transfer moieties have complementary sequences, such that they can hybridize together to form a bioconductor. In this embodiment, the hybridized duplex is capable of transferring at least one electron from the electron donor moiety to the electron acceptor moiety. In a preferred embodiment, the individual single stranded nucleic acids are aligned such that they have blunt ends; in alternative embodiments, the nucleic acids are aligned such that the double helix has cohesive ends. In either embodiment, it is preferred that there be uninterrupted double helix base-pairing between the electron donor moiety and the electron acceptor moiety, such that electrons may travel through the stacked base pairs.

In one bioconductor embodiment, the double stranded nucleic acid has one single strand nucleic acid which carries all of the electron transfer moieties. In another embodiment, the electron transfer moieties may be carried on either strand, and in any orientation. For example, one strand may carry only electron donors, and the other only electron acceptors or both strands may carry both.

In one embodiment, the double stranded nucleic acid may have different electron transfer moieties covalently attached in a fixed orientation, to facilitate the long range transfer of electrons. This type of system takes advantage of the fact that electron transfer species may act as both electron donors and acceptors depending on their oxidative state. Thus, an electron donor moiety, after the loss of an electron, may act as an electron acceptor, and vice versa. Thus, electron transfer moieties may be sequentially oriented on either strand of the double stranded nucleic acid such that directional transfer of an electron over very long distances may be accomplished. For example, a double stranded nucleic acid could contain a single electron donor moiety at one end and electron acceptor moieties, of the same or different composition, throughout the molecule. A cascade effect of electron transfer could be accomplished in this manner, which may result in extremely long range transfer of electrons.

The choice of the specific electron donor and acceptor pairs will be influenced by the type of electron transfer measurement used; for a review, see Winkler et al., Chem. Rev. 92: 369–379 (1992). When a long-lived excited state can be prepared on one of the redox sites, direct measurement of the electron transfer rate after photoinduction can be measured, using for example the flash-quench method of Chang et al., J. Amer. Chem. Soc. 113: 7057 (1991). In this preferred embodiment, the excited redox site, being both a better acceptor and donor than the ground-state species, can transfer electrons to or from the redox partner. An advantage of this method is that two electron transfer rates may be measured: the photoinduced electron transfer rates and thermal electron-hole recombination reactions. Thus differential rates may be measured for hybridized nucleic acids with perfect complementarity and nucleic acids with mismatches.

In alternative embodiments, neither redox site has a long lived excited state, and electron transfer measurements depend upon bimolecular generation of a kinetic intermediate. For a review, see Winkler et al., supra. This intermediate then relaxes to the thermodynamic product via intramolecular electron transfer using a quencher, as seen below:

$$D-A+h\nu \rightarrow D-A^*$$

$$D-A^*+Q \rightarrow D-A^++Q^-$$

$$D-A^+ \rightarrow D^+-A$$

$$D^+-A+Q^- \rightarrow D-A+Q$$

The upper limit of measurable intramolecular electron transfer rates using this method is about $10^4$ per second. Alternative embodiments use the pulse-radiolytic generation of reducing or oxidizing radicals, which inject electrons into a donor or remove electrons from a donor, as reviewed in Winkler et al., supra.

Electron transfer will be initiated using electrical, electrochemical, photon (including laser) or chemical activation of the electron transfer moieties. These events are detected by changes in transient absorption or by fluorescence or phosphorescence or chemiluminescence of the electron transfer moieties.

In the preferred embodiment, electron transfer occurs after photoinduction with a laser. In this embodiment, electron donor moieties may, after donating an electron, serve as electron acceptors under certain circumstances. Similarly, electron acceptor moieties may serve as electron donors under certain circumstances.

In a preferred embodiment, DNA is modified by the addition of electron donor and electron acceptor moieties. In an alternative embodiment, RNA is modified. In a further embodiment, a double stranded nucleic acid for use as a bioconductor will contain some deoxyribose nucleotides, some ribose nucleotides, and a mixture of adenosine, thymidine, cytosine, guanine and uracil bases.

In accordance with a further aspect of the invention, the preferred formulations for donors and acceptors will possess a transition metal covalently attached to a series of ligands and further covalently attached to an amine group as part of the ribose ring (2' or 3' position) or to a nitrogen or sulfur atom as part of a nucleotide dimer linked by a peptide bond, phosphoramidate bond, phosphorothioate bond, phosphorodithioate bond or O-methyl phosphoramidate bond.

Figure 4B:
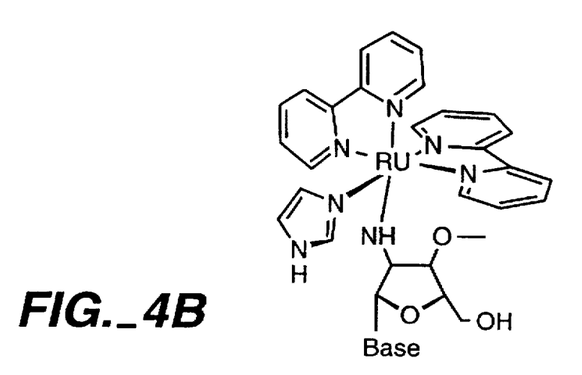
FIG. 4B depicts a specific example of a ruthenium electron transfer moiety using bisbipyridine and imidazole as the ligands.

A general formula is representative of a class of donors and acceptors that may be employed is shown in FIG. 4A. In this figure, M may be Cd, Mg, Cu, Co, Pd, Zn, Fe, Ru with the most preferred being ruthenium. The groups $R^1$, $R^2$, $R^3$, $R^4$, and $R^5$ may be any coordinating ligand that is capable of covalently binding to the chosen metal and may include ligands such as $NH_3$, pyridine, isonicotinamide, imidazole, bipyridine, and substituted derivative of bipyridine, phenanthrolines and substituted derivatives of phenanthrolines, porphyrins and substituted derivatives of the porphyrin family. The structure of a ruthenium electron transfer species using bisbipyridine and imidazole as the ligands is shown in FIG. 4B. Specific examples of useful electron transfer complexes include, but are not limited to, those shown in Table 1.

TABLE 1

| Donors | Acceptors |
| --- | --- |
| Ru(bpy)$_2$im—NH$_2$—U | Ru(NH$_3$)$_5$—NH$_2$—U |
| Ru(bpy)$_2$im—NH$_2$—U | Ru(NH$_3$)$_4$py—NH$_2$—U |
| Ru(bpy)$_2$im—NH$_2$—U | Ru(NH$_3$)$_4$im—NH$_2$—U |

Where:
Ru = ruthenium
bpy = bisbipyridine
im = imidazole
py = pyridine

It is to be understood that the number of possible electron donor moieties and electron acceptor moieties is very large, and that one skilled in the art of electron transfer compounds will be able to utilize a number of compounds in the present invention.

In an alternate embodiment, one of the electron transfer moieties may be in the form of a solid support such as an electrode. When the other electron transfer moiety is in solution the system is referred to as a heterogenous system as compared to a homogenous system where both electron donor and electron transfer moities are in the same phase.

The techniques used in this embodiment are analogos to the wiring of proteins to an electrode except that the nucleic acids of the present invention are used rather than a redox protein (see for example Gregg et al., J. Phys. Chem. 95: 5970 (1991); Heller et al., Sensors and Actuators R., 13–14: 180 (1993); and Pishko et al., Anal. Chem., 63: 2268 (1991)). In this embodiment, it is preferred that a redox polymer such as a poly-(vinylpyridine) complex of Os(bpy)$_2$Cl be cross-linked with an epoxide such as diepoxide to form a redox-conducting epoxide cement which is capable of strongly binding to electrodes made of conductive material such as gold, vitreous carbon, graphite, and other conductive materials. This strong attachment is included in the definition of "covalently attached" for the purposes of this embodiment. The epoxide cross-linking polymer is then reacted with. for example, an exposed amine, such as the amine of an amino-modified nucleic acid described above, covalently attaching the nucleic acid to the complex, forming a "redox hydrogel" on the surface of the electrode.

In this embodiment, a single stranded nucleic acid probe containing at least one electron transfer moiety is attached via this redox hydrogel to the surface of an electrode. Hybridization of a target sequence can then be measured as a function of conductivity between the electron transfer moiety covalently attached to one end of the nucleic acid and the electrode at the other end. This may be done using equipment and techniques well known in the art, such as those described in the references cited above.

In similar embodiments, two nucleic acids are utilized as probes as described previously. For example, one nucleic acid is attached to a solid electrode, and the other, with a covalently attached electron transfer moiety, is free in solution. Upon hybridization of a target sequence, the two nucleic acids are aligned such that electron transfer between the electron transfer moiety of the hybridized nucleic acid and the electrode occurs. The electron transfer is detected as outlined above, or by use of amperometric, potentiometric or conductometric electrochemical sensors using techniques well known in the art.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

The amino-modified monomer units are prepared by variation of published procedures and are incorporated into a growing oligonucleotide by standard synthetic techniques. The procedure is applicable to both DNA and RNA derivatives.

Example 1

Synthesis of an Oligonucleotide Duplex with Electron Transfer Moieties at the 5' Termini In this example an eight nucleotide double stranded nucleic acid was produced, with each single strand having a single electron transfer moiety covalently attached to the 5' terminal uridine nucleotide at the 2' carbon of the ribose sugar.

Step 1: Synthesis of 5'-di(p-methoxyphenyl)methyl ether-2'-(trifluoroacetamido)-2'-deoxyuridine 2'-(trifluoroacetamido)-2'-deoxyuridine (2.0 g, 5.9 mmoles) prepared by minor modification of published procedures (Imazawa, supra) was repeatedly dissolved in a minimum of very dry $CH_3CN$ and rotary evaporated to dryness and then transferred to inert atmosphere vacuum line and further dried for a period of 1 hour. The following procedure for the synthesis of the material was adapted from Gait (supra): Under positive pressure argon, the material was dissolved in freshly dried and distilled pyridine and with stirring, 0.05 equivalents (wt.) of 4-dimethylaminopyridine (DMAP), 1.5 equivalents of triethylamine (TEA) and 1.2 equivalents of 4,4'-dimethoxytrityl chloride (DMTr-Cl) were added to the reaction mixture. The progress of the reaction was monitored by silica gel TLC (98:2 methylene chloride:methanol, mobile phase). After 30 minutes, an additional 0.5 equivalents each of DMTr-Cl and TEA were added and the reaction allowed to proceed for an additional three hours. To this reaction mixture was added an equal volume of water and the solution extracted several times with diethyl ether. The ether layers were rotary evaporated to dryness, redissolved in a minimum amount of methylene chloride and purified by flash chromatography (99:1 methylene chloride:methanol, mobile phase), to obtain the 5'-di(p-methoxyphenyl)methylether-2'-(trifluoroacetamido)-2'-deoxyuridine product.

Step 2: 5'-2'-aminouridine-GCTACGA and 5'-2'-aminouridine-CGTAGCA

5'-di(p-methoxyphenyl)methyl ether-2'-(trifluoroacetamido)-2'-deoxyuridine was dried under reduced pressure (glass) and dissolved in freshly dried and distilled $CH_3CN$ and placed in a specially made conical vial and placed on an ABI DNA synthesizer. The program for the preparation of standard (i.e. unmodified) oligonucleotides was altered during the final base (amino-modified) addition to a 15-30 minute coupling time. The oligonucleotide was cleaved from the column by standard procedures and purified by C-18 reverse phase HPLC. In this manner 5'-2'-aminouridine-GCTACGA and 5'-2'-aminouridine-CGTAGCA were prepared. In addition, unmodified complementary strands to both products were made for use in the electron transfer moiety synthesis below.

Step 3: 5'-2'-ruthenium bisbipyridineimidazole-aminouridine-GCTACGA

5'-2'-aminouridine GCTACGA produced in the previous step was annealed to the complementary unmodified strand using standard techniques. All manipulations of the annealed duplex, prior to the addition of the transition metal complex were handled at 4° C. In order to insure that the DNA remained annealed during modification, the reactions were performed in 1M salt. The 5'-amino modified duplex DNA was dissolved in 0.2M HEPES, 0.8M NaCl, pH 6.8 and repeatedly evacuated on a Schlenk line. Previously prepared ruthenium bisbipyridine carbonate was dissolved in the above buffer and oxygen was removed by repeated evacuation and purging with argon via a Schlenk line. The ruthenium complex was transferred to the DNA solution via cannulation (argon/vacuum) and the reaction allowed to proceed under positive pressure argon with stirring for 24 hours. To this reaction, 50 equivalents of imidazole was added to the flask and the reaction allowed to proceed for an additional 24 hours. The reaction mixture was removed from the vacuum line and applied to a PD-10 gel filtration column and eluted with water to remove excess ruthenium complex. The volume of the collected fractions was reduced to dryness via a speed vac and the solid taken up in 0.1M triethylammonium acetate (TEAC) pH 6.0. The duplex DNA was heated to 60° C. for 15 minutes with 50% formamide to denature the duplex. The single stranded DNA was purified using a C-18 reverse phase HPLC column equiped with a diode array detector and employing a gradient from 3% to 35% acetonitrile in 0.1M TEAC, pH 6.0.

Step 4: 5'-2'-ruthenium tetraminepyridine-aminouridine-CGTAGCA

5'-aminouridine-CGTAGCA (0.3 µm) was dissolved in 0.2M HEPES, 0.8M NaCl buffer, pH 6.8 and degassed on the vacuum line. To a 10 ml conical shaped flask equipped with a stirring bar and septum was slurried Ru(III) tetraaminepyridine chloride (10 µm), in the same buffer. In a separate flask, Zn/Hg amalgam was prepared and dried under reduced pressure and the ruthenium(III) solution transferred (via cannulation) to the Zn/Hg amalgam. The immediate formation of a clear yellow solution ($\lambda_{max}$=406 nm) indicated that the reduced form of the ruthenium had been achieved and the reaction allowed to proceed for 30 minutes. This solution was transferred to the flask containing the amino-modified DNA and the reaction allowed to proceed at room temperature for 24 hours under argon. The reaction mixture was removed from the vacuum line and a 50 fold excess of cobalt EDTA (Kirschner, Inorganic Synthesis (1957), pp 186) added to the solution. The solution was applied to Sephadex G-25 gel filtration column to remove excess ruthenium complex and further purified by reverse phase HPLC as described above. The two ruthenium modified nucleotides were annealed by standard techniques and characterized (see Example 5).

Example 2

Synthesis of Long DNA Duplexes with Electron Transfer Moieties at the 5' Termini In this example, an in vitro DNA amplification technique, PCR (reviewed in Abramson et al., Curr. Op. in Biotech. 4: 41–47 (1993)) is used to generate modified duplex DNA by polymerization of nucleotides off modified primer strands (Saiki et al., Science 239: 487 (1988)). Two oligonucleotides 18 bases in length and not complementary to each other are synthesized with amino-modification to the 2'-ribose position of the 5' nucleotides, as in example 1.

A series of oligonucleotides of increasing lengths starting at 40 bases are chemically synthesized using standard chemistry. Each of the PCR templates shares a 5' sequence identical to one modified 18 mer. The 3' end of the template oligonucleotide shares a sequence complementary to the other 18 mer.

PCR rapidly generates modified duplex DNA by the catalysis of 5'-3' DNA synthesis off of each of the modified 18 mers using the unmodified strand as a template. One hundred nanomoles of each of the two modified 18 mers are mixed in 1 ml of an aqueous solution containing 2,000 units of Taq polymerase, deoxyribonucleoside triphosphates at 0.2M each, 50 mM KCl, 10 nM Tris-Cl, pH 8.8, 1.5 mM $MgCl_2$, 3 mM dithiothreitol and 0.1 mg/ml bovine serum albumin. One femtomole of the template strand 40 bases in length is added to the mixture. The sample is heated at 94° C. for one minute for denaturation, two minutes at 55° C. for annealing and three minutes at 72° C. for extension. This cycle is repeated 30 times using an automated thermal cycler.

The amplified template sequences with transition metal complexes on both 5' termini are purified by agarose gel electrophoresis and used directly in electron transfer applications.

Example 3

Synthesis of Covalently Bound Electron Transfer Moieties at Internucleotide Linkages of Duplex DNA In this example, alternative backbones to phophodiester linkages of oligonucleotides are employed. Functional groups incorporated into these internucleotide linkages serve as the site for covalent attachment of the electron transfer moieties. These alternate internucleotide linkages include, but are not limited to, peptide bonds, phosphoramidate bonds, phosphorothioate bonds, phosphorodithioate bonds and O-methylphosphoramidate bonds.

The preparation of peptide nucleic acid (PNA) follows literature procedures (See Engholm, supra), with the synthesis of Boc-protected pentaflurophenyl ester of the chosen base (thymidine). The resulting PNA may be prepared employing Merrifield's solid-phase approach (Merrifield, Science, 232: 341 (1986)), using a single coupling protocol with 0.1M of the thiminyl monomer in 30% (v/v) DMF in $CH_2Cl_2$. The progress of the reaction is followed by quantiative ninhydrin analysis (Sarin, Anal. Biochem., 117: 147 (1981)). The resulting PNA may be modified with an appropriate transition metal complex as outlined in example 1.

The synthesis of phosphoramidate (Beaucage, supra, Letsinger, supra, Sawai, supra) and N-alkylphosphoramidates (Jager, supra) internucleotide linkages follows standard literature procedures with only slight modification (the procedures are halted after the addition of a single base to the solid support and then cleaved to obtain a dinucleotide phosphoramidate). A typical example is the preparation of the phenyl ester of 5'O-isobutyloxycarbonylthymidyl-(3'-5')-5'-amino-5'-deoxythymidine (Letsinger, J. Org. Chem., supra). The dimer units are substituted for standard oligonucleotides at chosen intervals during the preparation of DNA using established automated techniques. Transition metal modification of the modified linkages takes place as described in Example 1.

The synthesis of phosphorothioate and phosphorodithioate (Eckstein, supra, and references within) internucleotide linkages is well documented. A published protocol utilizes an Applied Biosystems DNA synthesizer using a modified B-cyanoethylphosphoramidite cycle that caps after sulphurization with tetraethylthiuram disulfide (TETD) (Iyer, J. Org. Chem. 55: 4693 (1990)). The phosphorothioate and phosphorodithioate analogs are prepared as dimers and cleaved from the solid support and purified by HPLC (acetonitrile/triethylammonium acetate mobile phase).

Example 4

Synthesis of Two Oligonucleotides Each with an Electron Transfer .oiety at the 5' Terminus In this example, two oligonucleotides are made which hybridize to a single target sequence, without intervening sequences. One oligonucleotide has an electron donor moiety covalently attached to the 5' terminus, and the other has an electron acceptor moiety covalently attached to the 5' terminus. In this example, the electron transfer species are attached via a uradine nucleotide, but one skilled in the art will understand the present methods can be used to modify any of the nucleotides. In addition, one skilled in the art will recognize that the procedure is not limited to the generation of 8-mers, but is useful in the generation of oligonucleotide probes of varying lengths.

The procedure is exactly as in Example 1, except that the 8-mers generated are not complementary to each other, and instead are complementary to a target sequence of 16 nucleotides. Thus the final annealing step of step 4 of Example 1 is not done. Instead, the two modified oligonucleotides are annealed to the target sequence, and the resulting complex is characterized as in Example 5.

Example 5

Characterization of Modified Nucleic Acids
Enzymatic digestion

The modified oligonucleotides of example 1 were subjected to enzymatic digestion using established protocols and converted to their constituent nucleosides by sequential reaction with phosphodiesterase and alkaline phosphatase. By comparison of the experimentally obtained integrated HPLC profiles and UV-vis spectra of the digested oligonucleotides to standards (including 2'-aminouridine and 2'-aminoadenine), the presence of the amino-modified base at the predicted retention time and characteristic UV-vis spectra was confirmed. An identical procedure was carried out on the transition metal modified duplex DNA and assignments of constituent nucleosides demonstrated single-site modification at the predicted site.

Fluorescent labeled amino-modified oligonucleotides

It has been demonstrated that the fluorochrome, fluorescein isothiocyanate (FITC) is specific for labeling primary amines on modified oligonucleotides while not bonding to amines or amides present on nucleotide bases (Haugland, Handbook of Fluorescent Probes and Research Chemicals, 5th Edition, (1992)). This reaction was carried out using the amino-oligonucleotide synthesized as described in example 1 and on an identical bases sequence without the 2'-aminoribose group present. Fluorescence spectroscopic measurements were acquired on both these oligonucleotides and the results confirm the presence of the amine on the 5'-terminal ribose ring.

Thermodynamic Melting Curves of Modified Duplex DNA

A well established technique for measuring thermodynamic parameters of duplex DNA is the acquisition of DNA melting curves. A series of melting curves as a function of concentration of the modified duplex DNA was measured via temperature controlled UV-vis (Hewlett-Packard), using techniques well known in the art. These results confirm that hybridization of the amino-modified and transition metal modified DNA had taken place. In addition, the results indicate that the modified DNA form a stable duplex comparable to the stability of unmodified oligonucleotide standards.

Two Dimensional Nuclear Magnetic Resonance (NMR) Spectroscopy

The amino-modified oligonucleotides synthesized as a part of this work were prepared in sufficient quantities (6 micromoles) to permit the assignment of the $^1$H proton NMR spectra using a 600 MHz Varian NMR spectrometer.

Measurement of the rate of electron transfer

An excellent review of the measurement techniques is found in Winkler et al., Chem. Rev. 92: 369–379 (1992). The donor is Ru(bpy)$_2$(NHuridine)im, E$^0$~1 V, and the acceptor is Ru(NH$_3$)$_4$py(NHuridine)im, E$^0$~330 mV. The purified transition metal modified oligonucleotides (U$_{NHRu(bpy)}$2imGCATCGA and U$_{NHRu(NH3)4(py)im}$CGATGCA were annealed by heating an equal molar mixture of the oligonucleotides (30 µmolar: 60 nmoles of DNA in 2 ml buffer) in pH 6.8 (100 mM NaPi, 900 mM NaCl) to 60° C. for 10 minutes and slowly cooling to room temperature over a period of 4 hours. The solution was transferred to an inert atmosphere cuvette equipped with adapters for attachment to a vacuum line and a magnetic stirring bar. The solution was degassed several times and the sealed apparatus refilled repeatedly with Ar gas.

The entire apparatus was inserted into a cuvette holder as part of the set-up using the XeCl excimer-pumped dye laser and data acquired at several wavelengths including 360, 410, 460 and 480 nm. The photoinduced electron transfer rate is $1.6 \times 10^6$ S$^{-1}$ over a distance of 28 Å.

Example 6

Synthesis of a Single Stranded Nucleic Acid Labeled with Two Electron Transfer Moieties This example uses the basic procedures described earlier to generate two modified oligonucleotides each with an electron transfer moiety attached. Ligation of the two modified strands to each other produces a doubly labeled nucleic acid with any of four configurations: 5' and 3' labeled termini, 5' labeled terminus and internal nucleotide label, 3' labeled terminus and internal nucleotide label, and double internal nucleotide labels. Specifically, the synthesis of an oligonucleotide 24 bases in length with an electron transfer donor moiety on the 5' end and an internal electron transfer moiety is described.

Five hundred nanomoles of each of two 5'-labeled oligonucleotides 12 bases in length are synthesized as detailed above with ruthenium (II) bisbipyridine imidazole on one oligonucleotide, "D" and ruthenium (III) tetraamine pyridine on a second oligonucleotide, "A".

An unmodified oligonucleotide 24 bases in length and complementary to the juxtaposition of oligonucleotide "D" followed in the 5' to 3' direction by oligonucleotide "A" is produced by standard synthetic techniques. Five hundred nanomoles of this hybridization template is added to a mixture of oligonucleotides "A" and "D" in 5 ml of an aqueous solution containing 500 mM Tris-Cl, pH 7.5, 50 MM MgCl$_2$, 50 mM dithiothreitol and 5 mg/ml gelatin. To promote maximal hybridization of labeled oligonucleotides to the complementary strand, the mixture is incubated at 60° C. for 10 minutes then cooled slowly at a rate of approximately 10° C. per hour to a final temperature of 12° C. The enzymatic ligation of the two labeled strands is achieved with T4 DNA ligase at 12° C. to prevent the ligation and oligomerization of the duplexed DNA to other duplexes (blunt end ligation). Alternatively, E. coli DNA ligase can be used as it does not catalyze blunt end ligation.

One hundred Weiss units of T4 DNA ligase is added to the annealed DNA and adenosine triphosphate is added to a final concentration of 0.5 mM. The reaction which catalyzes the formation of a phosphodiester linkage between the 5' terminal phosphate of oligonucleotide "A" and the 3' terminal hydroxyl group of oligonucleotide "D" is allowed to proceed for 18 hours at 12° C. The reaction is terminated by heat inactivation of the enzyme at 75° C. for 10 minutes. The doubly labeled oligonucleotide is separated from the singly labeled oligonucleotides and the complementary unlabeled oligonucleotide by HPLC in the presence of urea as in the previous examples. The doubly labeled oligonucleotide of this example is ideally suited for use as a photoactive gene probe as detailed below.

Example 7

Use of a Doubly Modified Oligonucleotide with Electron Transfer Moieties as a Photoactive Probe for Detection of Complementary Nucleic Acid Sequence This example utilizes the oligonucleotide 24 mer of example 6 in a unique type of gene-probe assay in which removal of unhybridized probe prior to signal detection is not required. In the assay procedure, a region of the gag gene of human immunodeficiency virus type I (HIV-I) is amplified by the polymerase chain reaction (Saiki et al., Science 239: 487–491 (1988)). This region of HIV-I is highly conserved among different clinical isolates.

The amplified target DNA versus controls lacking in HIV-I DNA are added to a hybridization solution of 6XSSC (0.9M NaCl, 0.09M Na citrate, pH 7.2) containing 50 nanomoles of doubly labeled 24 mer probe of example 6. Hybridization is allowed to proceed at 60° C. for 10 minutes with gentle agitation. Detection of electron transfer following laser excitation is carried out as in example 5. Control samples which lack the hybridized probe show negligible electron transfer rates. Probes hybridized to the gag sequence show efficient and rapid electron transfer through the DNA double helix, providing a highly specific, homogeneous and automatable HIV-I detection assay.

A similar homogeneous gene probe assay involves the use of two probes, one an electron donor and the other an electron acceptor, which hybridize with the gag region of HIV-I in a tandem configuration, one probe abutting the other. In this assay, electronic coupling between the two electron transfer moieties depends entirely on hybridization with the target DNA. If appropriate, the electron transfer from one probe to the other is enhanced by the ligation of the juxtaposed ends using T4 DNA ligase as in example 6.

What is claimed is:

1. A composition comprising a first single stranded nucleic acid containing one or multiple electron transfer moieties and a second single stranded nucleic acid containing one or multiple electron transfer moieties, wherein said electron transfer moieties are transition metal complexes covalently linked to a ribose of the ribose-phosphate backbone of said first and second single stranded nucleic acids, and wherein electron transfer occurs between said electron transfer moieties when said first single stranded nucleic acid hybridizes to a first domain of a target sequence, said second single stranded nucleic acid hybridizes to a second domain of said target sequence, and an intervening nucleic acid hybridizes to an intervening target domain of said target sequence.

2. A composition comprising a first single stranded nucleic acid containing one or multiple electron transfer moieties and a second single stranded nucleic acid containing one or multiple electron transfer moieties, wherein one of said electron transfer moieties is an electrode and the other is a transition metal complex covalently attached to a ribose of the ribose-phosphate backbone of said nucleic acid, wherein electron transfer occurs between said electron transfer moieties when said first single stranded nucleic acid hybridizes to a first domain of a target sequence, said second single stranded nucleic acid hybridizes to a second domain of said target sequence, and an intervening nucleic acid hybridizes to an intervening target domain of said target sequence.

3. A composition according to claim 1 wherein said attachment is to the 2' position of said ribose.

4. A composition according to claim 1 wherein said attachment is to the 3' position of said ribose.

5. A composition according to claim 1 wherein there are no more than 5 unconjugated sigma bonds between said transition metal and the base attached to said ribose.

6. A composition according to claim 1 wherein there are no more than 4 unconjugated sigma bonds between said transition metal and the base attached to said ribose.

7. A single stranded nucleic acid containing one or multiple electron donor moieties and one or multiple electron acceptor moieties, wherein said electron donor and acceptor moieties are transition metal complexes covalently attached to the ribose-phosphate backbone of said nucleic acid, wherein one or multiple of said transition metal complexes is covalently attached via a modified nucleotide dimer, and wherein electron transfer can occur between said electron donor and acceptor moieties when said single stranded nucleic acid is hybridized to a target sequence.

8. A single stranded nucleic acid containing one or multiple electron donor moieties and one or multiple electron acceptor moieties, wherein one of said electron transfer moieties is an electrode and the other is a transition metal complex covalently attached via a modified nucleotide dimer, and wherein electron transfer can occur between said electron donor and acceptor moieties when said single stranded nucleic acid is hybridized to a target sequence.

9. A single stranded nucleic acid according to claim 7 or 8, wherein said modified nucleotide dimer contains a phosphoramide linkage.

10. A single stranded nucleic acid according to claim 7 wherein one or multiple of said transition metal complexes is covalently attached via a ribose of the ribose-phosphate backbone.

11. A composition comprising a first single stranded nucleic acid containing one or multiple electron transfer moieties and a second single stranded nucleic acid containing one or multiple electron transfer moieties, wherein each of said electron transfer moieties is a transition metal complex covalently attached to a ribose of the ribose-phosphate backbone of said first and second single stranded nucleic acids, and wherein electron transfer occurs between said electron transfer moieties when said first single stranded nucleic acid is hybridized to said second single stranded nucleic acid.

12. A composition comprising a first single stranded nucleic acid containing one or multiple electron transfer moieties and a second single stranded nucleic acid containing one or multiple electron transfer moieties, wherein one of said electron transfer moieties is an electrode and the other is a transition metal complex covalently attached to the ribose-phosphate backbone of said nucleic acid, and wherein electron transfer occurs between said electron transfer moieties when said first single stranded nucleic acid is hybridized to said second single stranded nucleic acid.

13. A method of making a single stranded nucleic acid containing one or multiple electron donor moieties and one or multiple electron acceptor moieties, wherein said electron donor and acceptor moieties are transition metal complexes covalently attached to the ribose-phosphate backbone of said nucleic acid, wherein electron transfer can occur between said electron donor and acceptor moieties when said single stranded nucleic acid is hybridized to a target sequence, said method comprising a) incorporating a modified nucleotide to form a modified single stranded nucleic acid.

14. A method according to claim 13 further comprising b) hybridizing said modified nucleic acid with a complementary single stranded nucleic acid to form a double stranded nucleic acid.

15. A method according to claim 13 or 14 further comprising c) reacting said modified nucleotide with an electron transfer moiety such that said moiety is covalently attached to said modified nucleotide.

16. A method according to claim 13 wherein said modified nucleotide is an amino-modified nucleotide.

17. A method according to claim 16 wherein said amino-modified nucleotide is a 2' amino modified nucleotide.

18. A method according to claim 16 wherein said amino-modified nucleotide is a 3' amino modified nucleotide.

19. A method according to claim 13 wherein said modified nucleotide is a modified nucleotide dimer.

20. A method according to claim 13 wherein said incorporation is via standard synthetic techniques.

21. A method according to claim 13 wherein said incorporation is via enzymatic addition.

* * * * *